United States Patent [19]

Benardella

[11] Patent Number: Plant 5,925

[45] Date of Patent: Apr. 7, 1987

[54] ROSE PLANT—BENBLACK

[75] Inventor: Frank A. Benardella, Old Tappen, N.J.

[73] Assignee: Nor'East Miniature Roses, Inc., Rowley, Mass.

[21] Appl. No.: 738,295

[22] Filed: May 28, 1985

[51] Int. Cl.[4] ..... A01H 5/00

[52] U.S. Cl. ..... Plt./10

[58] Field of Search ..... Plt./10

*Primary Examiner*—Robert E. Bagwill

*Attorney, Agent, or Firm*—Vincent G. Gioia

[57] ABSTRACT

A new miniature rose variety of very dark red flower coloring and good exhibition form.

1 Drawing Figure

The present invention relates to a new and distinct variety of rose plant of the miniature rose class, which was originated by my crossing as seed parent the rose known as "Sheri Ann" (U.S. Plant Pat. No. 3,826) and as pollen parent the rose known as "Laguna". The varietal denomination of this new variety is "Benblack".

Among the novel characteristics possessed by this new variety which distinguish it from its parents and all other varieties of which I am aware are its unusually red flowers that maintain their color and form upon aging. Flowers are long lasting on the plant and as cut flowers. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "187A" is plate 187A of The Royal Horticultural Society Colour Chart.

Parentage: Seedling.

*Seed parent.*—"Sheri Ann".

*Pollen parent.*—"Laguna".

Class: Miniature.

The following observations are made of specimens grown under glass in Essex County, Mass., during the month of March.

FLOWER

Blooming habit: Recurrent.

A. Bud:

(1) *Size.*—Medium.

(2) *Form.*—Short pointed.

(3) *Color.*—When sepals first divide — dark red near between 187A to 187C. When petals begin to unfurl — near 187A to B, reverse near 187C.

(4) *Sepals.*—Longer than bud, thin, some foliated.

(5) *Peduncle.*—Length — about 1¼". Aspect — straight. Strength — erect. Color — near 148B.

B. Bloom:

(1) *Size.*—Average size when fully expanded — about 1¼ to 1½ inches.

(2) *Borne.*—Singly and several together in sprays.

(3) *Form.*—Cupped, then very full. High centered at first, becoming flat, outer petals reflex sharply and roll under upon opening.

(4) *Petalage.*—Number of petals under normal conditions — about 18.

(5) *Color.*—After sepals fall, visible flower coloring is very dark red 187A with little color difference at petal top and undersurface although undersurface may be a shade lighter. Color is stable as petals unfurl between 53A and 185A through to maturity. However, under bright light, color may appear lighter, i.e., 45B. General tonality from a distance is very dark red. Color at point of petal attachment is near 11B.

C. Petals:

(1) *Texture.*—Thick.

(2) *Appearance.*—Inside — very velvety, outside — satiny.

(3) *Form.*—Wedge shaped, apex pointed; outer petals reflex pointed, inner petals roll under at edges.

(4) *Arrangement.*—Regularly arranged, imbricated.

(5) *Petaloids in center.*—Few.

(6) *Persistence.*—Hang on.

(7) *Fragrance.*—Slight.

(8) *Lasting quality.*—Long lasting on plant and long lasting as cut flower.

REPRODUCTIVE ORGANS

A. Stamens, filaments and anthers:

(1) *Arrangement.*—Regular arrangement around styles.

(2) *Color.*—Near 14A.

B. Pollen:

*Color.*—Near 163B.

C. Styles: Medium length.

D. Stigmas:

*Color.*—Near 196A.

E. Hips: Globular, about ⅝ to ¾ inch; near 24A.

PLANT

A. Form: Upright, spreading.

B. Growth: Very vigorous.

*Height attained.*—About 15 to 20 inches.

C. Foliage: Compound 5 to 7 leaflets.

(1) *Size.*—Medium.

(2) *Quantity.*—Abundant.

(3) *Color.*—New foliage: Upper side — near to 144A with near 183B overlay. Under side — near to 146B Old foliage: Upper side — near 137A Under side — near 147B.

(4) *Shape.*—Oval, pointed.

(5) *Texture.*—Upper side is glossy and under side is matte.

(6) *Edge.*—Serrated.

(7) *Serration.*—Moderate.

(8) *Leaf stem.*—Color — near 200D. Under side — near 199C.

(9) *Stipules.*—Medium.

(10) *Resistance to disease.*—Blackspot — average. Mildew — average. Rust — average.

D. Wood:

(1) *New wood.*—Color — near 144B. Bark — smooth.

(2) *Old wood.*—Color — near 144A. Bark — smooth.

E. Thorns:

(1) *Thorns.*—Quantity (main stalk) — ordinary. On laterals from stalk — few. Form — sharp, pointed, curved slightly downward. Length — medium. Color — near 185B. Position — irregular.

(2) *Prickles.*—None.

F. Winter hardiness: Requires ordinary protection in extreme climates.

I claim:

1. A new and distinct variety of rose plant of the miniature rose class, substantially as shown and described, characterized particularly by unusually dark red flowers that hold color well through development and aging.

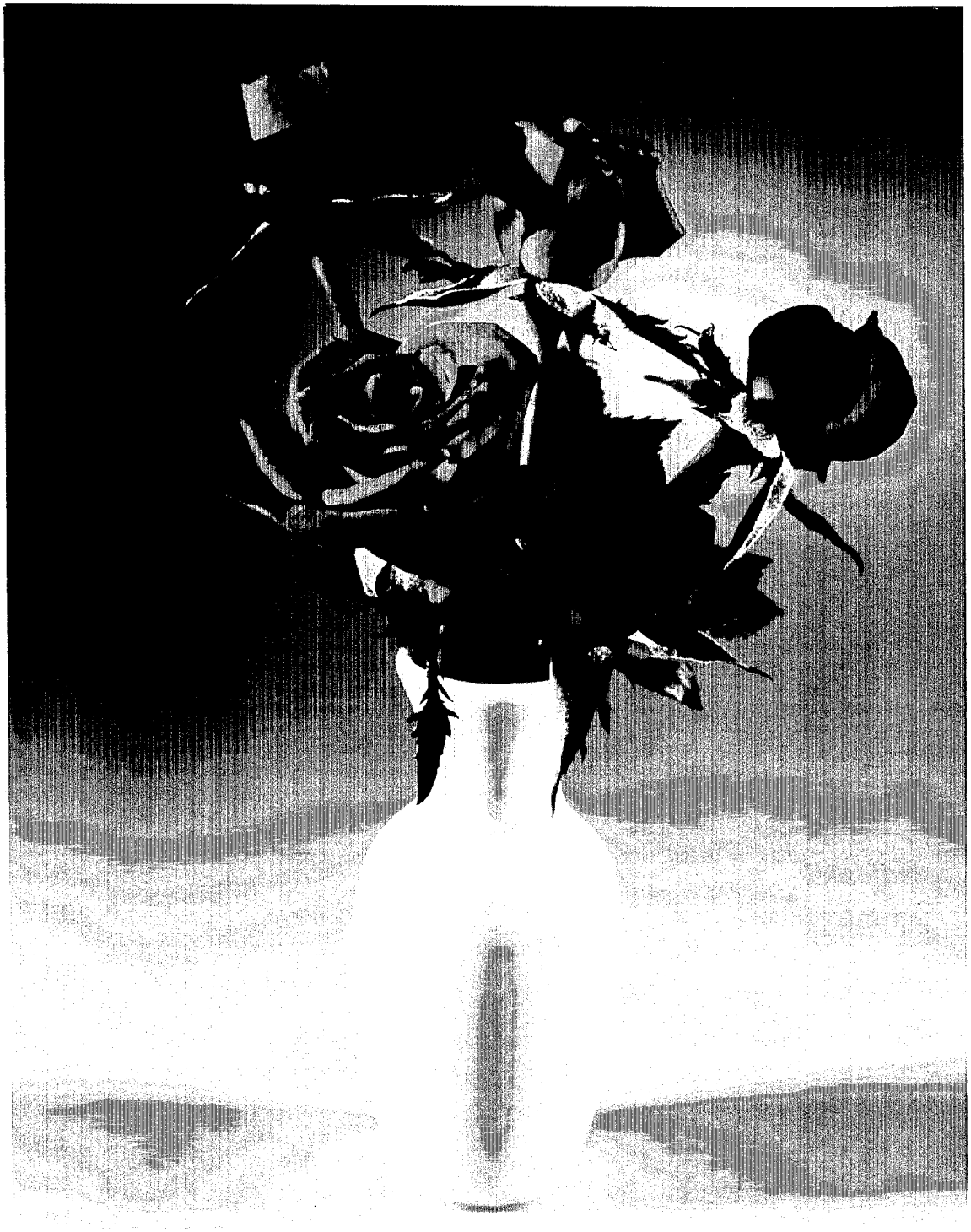

* * * * *